US006720295B2

(12) United States Patent
Vanhessche et al.

(10) Patent No.: US 6,720,295 B2
(45) Date of Patent: Apr. 13, 2004

(54) USE OF TERTIARY ALCOHOLS OR ESTERS AS PERFUMING INGREDIENTS

(75) Inventors: Koenraad Vanhessche, Hoboken, NJ (US); Jean-Marc Gaudin, Annemasse (FR); George Lem, New York, NY (US); Györgyi Sneyers, West Orange, NJ (US)

(73) Assignee: Firmenich SA, Geneva (CH)

( * ) Notice: Subject to any disclaimer, the term of this patent is extended or adjusted under 35 U.S.C. 154(b) by 14 days.

(21) Appl. No.: 10/224,568

(22) Filed: Aug. 19, 2002

(65) Prior Publication Data

US 2003/0087775 A1 May 8, 2003

Related U.S. Application Data

(60) Provisional application No. 60/318,695, filed on Sep. 10, 2001.

(30) Foreign Application Priority Data

Aug. 27, 2001 (WO) ................................ PCT/IB01/01541

(51) Int. Cl.[7] ........................... C11D 3/50; C07C 35/06; C07C 43/162; C07C 43/115

(52) U.S. Cl. ....................... 510/101; 568/838; 568/579; 568/667

(58) Field of Search .......................... 510/101; 568/838, 568/667, 579

(56) References Cited

U.S. PATENT DOCUMENTS 4,701,278 A 10/1987 Fehr ........................... 252/132

OTHER PUBLICATIONS

G. S. Skinner et al., Journal of the American Chemical Society 1954, vol. 76, pp. 3200–3203, Jun. 1954.*

Okazawa et al., "Solution carbocation stabilities measured by internal competition for a hydride ion", Canadian Journal of Chemistry, vol. 60, pp. 2180–2193 (1982).

* cited by examiner

*Primary Examiner*—John Hardee
(74) *Attorney, Agent, or Firm*—Winston & Strawn LLP

(57) ABSTRACT

Compounds of the formula (I)

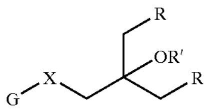

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group are disclosed for use as perfuming ingredients and perfumed articles or in perfuming compositions that contain such compounds.

12 Claims, No Drawings

USE OF TERTIARY ALCOHOLS OR ESTERS AS PERFUMING INGREDIENTS

This application claims the priority of International application no. PCT/IB01/01541 filed Aug. 27, 2001 and U.S. provisional application 60/318,695 filed Sep. 10, 2001.

TECHNICAL FIELD

The present invention relates to certain alcohol and ester compounds that are useful in perfumery as perfuming ingredients, in perfumed articles or in perfuming compositions. Specifically, the invention relates to uses of compounds of formula (I)

(I)

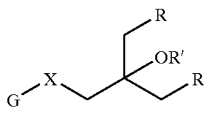

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group. The perfuming compositions, perfuming compositions and perfumed products contain one of the compounds of formula (I) as an active ingredient, usually together with perfume co-ingredients, solvents or adjuvants of current use in perfumery.

BACKGROUND OF THE INVENTION

Among the compounds encompassed by formula (I), only 4-cyclopentyl-2-methyl-2-butanol possesses a previously known structure. That compound has been described by Okazawa et al. in Can. J. Chem., (1982), 60, 2180. However, this prior art document mentions only the synthesis of 4-cyclopentyl-2-methyl-2-butanol and does not report or suggest any utility or use of the compound in the field of perfumery.

The odor properties of the compounds of formula (I) appear as totally unexpected also in view of the fact that compounds having an unsubstituted cyclopentyl or cyclopentenyl moiety and which are useful for perfumery are rare.

SUMMARY OF THE INVENTION

The invention relates to a perfuming composition or a perfumed product comprising as active ingredient a compound of formula (I)

(I)

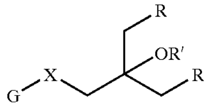

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, together with at least one perfuming co-ingredient, solvent or adjuvant of current use in perfumery.

Preferably, the perfuming ingredient is a compound of formula (II)

(II)

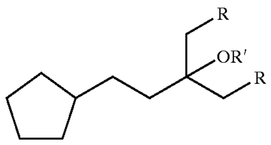

wherein the R groups represent, simultaneously or independently, a hydrogen atom or a methyl group and R' represents a hydrogen atom or an acetyl group. More preferred compounds include 4-cyclopentyl-2-methyl-2-butanol, 3-cyclopentyl-1,1-dimethylpropyl acetate or 5-cyclopentyl-3-ethyl-3-pentanol.

The perfuming composition or a perfumed product is generally in the form of a perfume or a cologne, a perfumed soap, a shower or bath gel, a shampoo, a body deodorant or antiperspirant, an ambient air deodorant, a liquid or solid detergent for textile treatment, a detergent composition or a cleaning product for dishes or various surfaces, a fabric softener or a cosmetic preparation.

The invention also relates to a method to impart, enhance, improve or modify the odor properties of a perfuming composition or a perfumed product which method comprises adding to said composition or product as a perfuming ingredient a compound of formula (I)

(I)

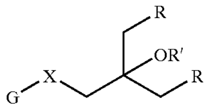

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, in an amount sufficient to impart, enhance, improve or modify the odor thereof with floral notes.

The invention also discloses new compounds, such as those of formula (I)

(I)

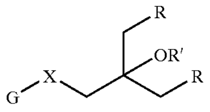

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, provided that 4-cyclopentyl-2-methyl-2-butanol is excluded. The most preferred of these are include 4-cyclopentyl-2-methyl-2-butanol, 3-cyclopentyl-1,1-dimethylpropyl acetate or 5-cyclopentyl-3-ethyl-3-pentanol.

DETAILED DESCRIPTION OF THE PREFERRED EMBODIMENTS

Surprisingly, we have now established that the compounds of formula (I)

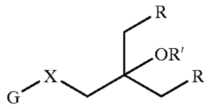

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group; possess very useful and appreciated odorant properties, of the floral type, which render them very convenient for the preparation of perfumes, perfuming compositions and perfumed articles.

As examples of preferred compounds of formula (I) one can cite 4-(2-cyclopenten-1-yl)-2-methyl-2-butanol and 1-(cyclopentyloxy)-2-methyl-2-propanol. Although the typical floral note of the invention compounds characterizes both compounds, each of them has additional and specific odor notes. For instance, 4-(2-cyclopenten-1-yl)-2-methyl-2-butanol also possesses fruity and vegetable, tomato leaves type notes which render its scent fruitier and stronger than the odor of 4-cyclopentyl-2-methyl-2-butanol described below, while 1-(cyclopentyloxy)-2-methyl-2-propanol scent also possesses a woody-terpineol note.

The most preferred compounds of formula (I) are those of formula (II)

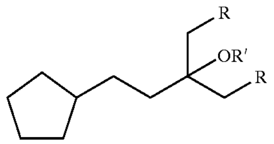

in which the R groups represent, simultaneously or independently, a hydrogen atom or a methyl group and R' represent a hydrogen atom or an acetyl group. Most preferably, the R groups represent a hydrogen atom.

Amongst the compounds of formula (II), 4-cyclopentyl-2-methyl-2-butanol, 3-cyclopentyl-1,1-dimethylpropyl acetate and 5-cyclopentyl-3-ethyl-3-pentanol are very much appreciated for the their excellent floral note.

4-Cyclopentyl-2-methyl-2-butanol, which is a preferred compound between those of formula (II), is highly appreciated for its ethereal, floral notes and more specifically for its powerful and fusing white flower, i.e. lily of the valley, note. When the odor of 4-cyclopentyl-2-methyl-2-butanol is compared with the one of 4-cyclohexyl-2-methyl-2-butanol (Firmenich SA ; U.S. Pat. No. 4,701,278) it appears that the former possesses a stronger top-note and impact and is closest to the odor of the lily of the valley flowers than the latter. Moreover, the 4-cyclopentyl-2-methyl-2-butanol odor is devoid of the coriander note present in the 4-cyclohexyl-2-methyl-2-butanol scent.

On the whole, the 4-cyclopentyl-2-methyl-2-butanol fragrance is similar to that of linalool but with a fresher and more pronounced lily of the valley connotation. Furthermore, the odor of 4-cyclopentyl-2-methyl-2-butanol has also a persistence in compositions, or on skin or hair, which is far superior to that of linalool.

A second preferred compounds of formula (II) is 3-cyclopentyl-1,1-dimethylpropyl acetate which possesses a lily of the valley, linalool-like fragrance with a character in between that of dihydroterpinyl acetate (origin: IFF, USA) and linalyl acetate, i.e. a floral-linalool scent with a nice fruity and citrus character.

Another compounds of formula (II) is 5-cyclopentyl-3-ethyl-3-pentanol which in addition to the floral, linalool-like notes, develops a fragrance with tea, and fruity-type notes, in particular grapefruit and strawberry-type bottom note, as well as basilic and parsley notes.

The compounds of the invention are suitable for use in fine perfumery, in perfumes, colognes or after-shave lotions, as well as in other current uses in perfumery such as to perfume soaps, preparations for the shower or the bath, such as bath salts, mousses, oils, gels or other preparations, products such as body oils, body-care products, body deodorants and antiperspirants, hair care products such as shampoos, ambient air deodorants, or cosmetic preparations.

The compounds of formula (I) can also be used in applications such as liquid or solid detergents for textile treatment, fabric softeners, or also in detergent compositions or cleaning products for cleaning dishes or varied surfaces, for industrial or household use.

In these applications, which are also an object of the invention, the compounds of formula (I) can be used alone, as well as mixed with other perfuming ingredients, solvents or additives commonly used in perfumery. The nature and variety of these co-ingredients do not require a more detailed description here, which would not be exhaustive anyway. In fact, a person skilled in the art, having a general knowledge, is able to choose them according to the nature of the product that has to be perfumed and the olfactory effect sought. These perfuming co-ingredients belong to varied chemical groups such as alcohols, aldehydes, ketones, esters, ethers, acetates, nitrites, terpenic hydrocarbons, heterocyclic nitrogen- or sulfur-containing compounds, as well as natural or synthetic essential oils. Many of these ingredients are listed in reference texts such as S. Arctander, Perfume and Flavor Chemicals, 1969, Montclair, N.J., USA, or more recent versions thereof, or in other similar books, or yet in the specialized patent literature commonly available in the art.

The proportions in which the compounds according to the invention can be incorporated in the different products mentioned above vary in a broad range of values. These values depend on the nature of the product that has to be perfumed and on the olfactory effect sought, as well as on the nature of the co-ingredients in a given composition when the compounds of the invention are used in admixture with perfuming co-ingredients, solvents or additives commonly used in the art.

For instance, concentrations from 1% to 20%, and preferably from 5% to 10%, by weight of these compounds, with respect to the perfuming composition in which they are incorporated, can be typically used. Much lower concentrations than these can be used when these compounds are directly applied for perfuming some of the consumer products mentioned above.

EXAMPLES

The invention will now be described in further details by way of the following examples, wherein the temperatures are indicated in degrees centigrade (° C.); the NMR spectral data were recorded with a 360 MHz machine in $CDCl_3$, the chemical displacement δ are indicated in ppm with respect to the TMS as standard and all the abbreviations have the usual meaning in the art. All experiments were conducted under a nitrogen atmosphere.

Example 1

Synthesis of 4-cyclopentyl-2-methyl-2-butanol 262.25 g (1.6 mol) of 3-cyclopentylpropionyl chloride (origin: Aldrich) and 500 ml of anhydrous THF (tetrahydrofuran) were charged into a 5 1 4-neck round bottom flask equipped with a mechanical stirrer and a reflux condenser. Upon cooling to 5° C., 3.2 1 of 1.4 M methyllitium in ether (4.48 mol) was added dropwise to the stirred solution at a rate which maintained the pot temperature between 15–25° C. The reaction mixture was then stirred at room temperature for 26 h and subsequently quenched, at 5° C., with the addition of 350 ml of water. The organic layer was separated and the ether and THF were stripped at reduced pressure. The resulting crude product was fractionally distilled with a 10-plate Oldershaw column at high vacuum to give 162 g of 4-cyclopentyl-2-methyl-2-butanol (purity>97%; yield=65%).

$^{1}$H-NMR: 1.08(m, 2H); 1.2(s, 6H); 1.35(m, 2H); 1.6(m, 1H, 4H, 4H); 1.8(s, 1H).

$^{13}$C-NMR: 25.24; 29.2; 30.82; 32.79; 40.60; 43.17; 70.95.

Example 2

Synthesis of 5-cyclopentyl-3-ethyl-3-pentanol 31.3 ml of a 2.8 M solution of EtMgCl in THF (87.7 mmol), diluted with 50 ml of anhydrous ether were placed into a 250 ml 4-neck round bottom flask, equipped with a mechanical stirrer and a reflux condenser. Upon cooling to 15–20° C., 6 g (35.16 mmol) of 3-cyclopentylpropionic acid ethyl ester (obtained according to Barret et al., *J. Chem. Soc.;* 1935, 1065) dissolved into 50 ml of anhydrous ether were added dropwise to the stirred solution at a rate which maintained the pot temperature between 15–25° C. The reaction mixture was then stirred at room temperature overnight and then quenched at 5° C. with the addition of 60 ml of water and neutralized at pH 7. The organic layer was separated and the ether and THF were stripped at reduced pressure. The resulting crude product was fractionally distilled with a bulb-to-bulb distillation (0.5 mbar, 120° C.) to give 4.5 g of pure 5-cyclopentyl-3-ethyl-3-pentanol (66% yield).

$^{1}$H-NMR: 0.86(t, 6H); 1.08(m, 3H); 1.27(m, 2H); 1.45(q, 4H); 1.50(m, 5H); 1.60(m, 1H); 1.70(m, 1H); 1.77(m, 2H).

$^{13}$C-NMR: 7.77; 25.22; 29.86; 31.04; 32.81; 37.22; 40.68; 74.58.

Example 3

Synthesis of 3-cyclopentyl-1,1-dimethylpropyl acetate 10 g (64 mmol) of 4-cyclopentyl-2-methyl-2-butanol, 32.6 g (320 mmol) of acetic anhydride and a drop of $H_3PO_4$ (85% in water) were introduced in a 200 ml flask, and the mixture was stirred over night, at room temperature. Afterwards, 100 ml of water where added and the stirring was prolonged for an additional period of 2 hours. The crude product was extracted by washing the water solution with pentane. The organic phases thus obtained were washed twice with a saturated $NaHCO_3$ water solution, then twice with brine and finally dried over $MgSO_4$ and concentrated. It was thus obtained 12.7 g of crude product (quantitative yield) having a GC purity of 99%.

$^{1}$H-NMR: 1.07(m, 2H); 1.30(m, 2H); 1.41(s, 6H); 1.50(m, 2H); 1.59(m, 2H); 1.73(m, 5H); 1.96(m, 3H).

$^{13}$C-NMR: 22.5(q); 25.2(2×t); 26.1(2×q); 30.3(t); 32.7(2×t); 39.9(d); 40.3(t) 40.3(d); 82.5(s); 170.5(s).

Example 4

Synthesis of 4-(2-cyclopenten-1-yl)-2-methyl-2-butanol 5.3 g (40.6 mmol) of 3-(2-chloroethyl)-1-cyclopentene (obtained according to Hill et al. in J. Org. Chem., 1969, 3681), dissolved into 30 ml of dry THF, were added dropwise into a three necks 200 ml flask containing 1.2 g (48.7 mmol) of magnesium and 5 ml of dry THF. After a 2 hours stirring at room temperature, 2.8 g (48.7 mmol) of acetone were slowly added to the reaction mixture. 15 Minutes after the addition of the acetone, the reaction mixture was slowly hydrolysed using 1 M aqueous HCl, and extracted with ether. Then, the organic phase was washed twice with water and twice with brine, dried over $MgSO_4$ and concentrated. The crude product was purified by chromatography over silica (eluant: cyclohexane/ethyle acetate=9/1). It was thus obtained 2.7 g of the title compound (yield=47%).

$^{1}$H-NMR: 1.21(s, 6H); 1.42(br, OH); 1.30–1.55(m, 4H); 2.05(m, 2H); 2.31(m, 2H); 2.62(m, 1H); 5.70(m, 2H).

$^{13}$C-NMR: 29.2(2×q); 29.8(t); 30.7(t); 32.0(t); 42.1(t); 45.8 (d); 71.0(s); 130.4(d); 135.0(d).

Example 5

Synthesis of 1-(cyclopentyloxy)-2-methyl-2-propanol and 3-[(cyclopentyloxy)methyl]-3-pentanol Synthesis of Methyl (Cyclopentyloxy)acetate:

In a three necks 500 ml flask were introduced, in the following order, 65 g (451 mmol) of (cyclopentyloxy)acetic acid (obtained according to U.S. Pat. No. 4,735,932), 1.4 g of para-toluenesulfonic acid and 280 ml of MeOH. After 6 hours at reflux, the reaction mixture was cooled at room temperature diluted into 300 ml of water and extracted with 300 ml of ether. The organic phase thus obtained was washed twice with water, dried over $MgSO_4$ and concentrated. It was thus obtained 56.9 g of product (yield=80%) having a GC purity of 99%.

$^{1}$H-NMR: 1.53(m, 2H); 1.72(m, 6H); 3.75(s, 3H); 4.00(m, 1H); 4.06(s, 2H).

$^{13}$C-NMR: 23.5(2×t); 32.1(2×t); 51.8(q); 66.4(t); 82.5(d); 171.2(s).

Synthesis of 1-(cyclopentyloxy)-2-methyl-2-propanol:

In a three necks 500 ml flask containing 200 ml of dry ether were introduced 26.5 ml (79 mmol) of a 3 M THF solution of MeMgCl and the mixture was cooled at 0° C. Then, while maintaining the mixture temperature below 10° C., were introduced dropwise 5 g (32 mmol) of methyl (cyclopentyloxy)acetate. 10 Minutes after the end of the addition, the reaction mixture was allowed to warm-up up to room temperature and then stirred for 2 hours. The reaction was then poured into an icy 2 M HCl aqueous solution and the organic phase was separated. The organic phase thus obtained was washed twice with water, dried over $MgSO_4$ and concentrated. It was thus obtained 3.9 g of crude product (yield=78%) having a GC purity of 99%.

$^{1}$H-NMR: 1.18(s, 6H); 1.52(m, 2H); 1.68(m, 6H); 2.45(s, OH); 3.20(m, 2H); 3.92(m, 1H).

$^{13}$C-NMR: 23.5(2×t); 26.1(2×q); 32.2(2×t); 70.0(s); 76.9(t); 81.9(d).

Synthesis of 3-[(cyclopentyloxy)methyl]-3-pentanol:

By applying an experimental procedure identical to the one hereinabove, but using the appropriate volume of a 3 M THF solution of EtMgCl, it was obtained the title compound with the same yield and purity as above.

Odour: floral, linalool $^{1}$H-NMR: 0.86(t, J=6 Hz, 6H); 1.48(q, J=6 Hz, 2H); 1.49(q, J=6 Hz, 2H); 1.5(m, 2H); 1.67(m, 6H); 2.21(s, OH); 3.22(s, 2H); 3.88(m, 1H).

$^{13}$C-NMR: 7.8(2×q); 23.5(2×t); 28.4(2×t); 32.2(2×t); 73.4 (t); 73.9(s); 81.8(d).

Example 6

A "herbaceous-citrus" type cologne for men was prepared by admixing the following ingredients:

| Ingredient | Parts by weight |
|---|---|
| 10%* Hexyl acetate | 10 |
| Citronellyl acetate | 10 |
| Geranyl acetate | 15 |
| Styrallyl acetate | 5 |
| Vetyveryl acetate | 70 |
| 10%* Aldehyde C 10[1)] | 10 |
| 1%* Aldehyde C 11 undecylic[1)] | 10 |
| 10%* Allyl amyl glycolate | 25 |
| 10%* Ambrox ®[2)] | 35 |
| Anethol | 5 |
| Bergamot essential oil | 700 |
| Cashmeran ®[3)] | 20 |
| 10%* Ciste essential oil | 20 |
| Sfuma lemon essential oil | 160 |
| Citronellol | 30 |
| Coumarine | 25 |
| Allyl(cyclohexyloxy)acetate | 5 |
| 10%* Damascenone[4)] | 10 |
| 10%* α-Damascone[5)] | 20 |
| Geranium essential oil | 5 |
| Habanolide ®[6)] | 500 |
| Helvetolide ®[7)] | 340 |
| Hedione ® HC[8)] | 300 |
| Heliopropanal | 60 |
| Iso E Super[9)] | 550 |
| Lavandin essential oil | 60 |
| Lilial ®[10)] | 50 |
| Mandarine essential oil | 100 |
| Patchouli essential oil | 30 |
| Pepper essential oil | 10 |
| Polysantol ®[11)] | 70 |
| 10%* Red thyme essential oil | 10 |
| Vanilline | 15 |
| 10%* Triplal[9)] | 70 |
| Galbex ®[1)] 183 | 15 |
| Santal essential oil | 30 |
| | 3400 |

*in dipropyleneglycol
[1)]origin: Firmenich SA, Geneva, Switzerland
[2)]dodecahydro-3a,6,6,9a-tetramethyl-nathptho[2,1-b]furan; origin: Firmenich SA, Geneva, Switzerland
[3)]1,2,3,5,6,7-hexahydro-1,1,2,3,3-pentamethyl-4-indenone; origin: IFF, USA
[4)]1-(2,6,6-trimethyl-1,3-cyclohexadien-1-yl)-2-buten-1-one; origin: Firmenich SA, Geneva, Switzerland
[5)]1-(2,6,6-trimethyl-2-cyclohexen-1-yl)-2-buten-1-one; origin: Firmenich SA, Geneva, Switzerland
[6)]pentadecenolide; origin: Firmenich SA, Geneva, Switzerland
[7)](+)-(1S,1'R)-2-[1-(3',3'-dimethyl-1'-cyclohexyl)ethoxy]-2-methylpropyl propanoate; origin: Firmenich SA, Geneva, Switzerland
[8)]methyl dihydrojasmonate; origin: Firmenich SA, Geneva, Switzerland
[9)]origin: IFF, USA
[10)]origin: Givaudan, Vernier, Switzerland
[11)]3,3-dimethyl-5-(2',2',3'-trimethyl-3'-cyclopenten-1'-yl)-4-penten-2-ol; origin: Firmenich SA, Geneva, Switzerland The addition of 900 parts by weight of 4-cyclopentyl-2-methyl-2-butanol imparts to the above-mentioned base composition a superb floral, lily of the valley, magnolia note which exalts the Hedione® notes and imparts to the perfume a floral, long-lasting trail. Said trail lasts for more than 6 hours, in contrast with similar notes imparted by well-known ingredients such as linalool, ethyl linalool, tetralinalool, dihydromyrcenol, etc.

Example 7

A "floral-musky-citrus" type perfuming base for detergents was prepared by admixing the following ingredients:

| Ingredient | Parts by weight |
|---|---|
| Terpenyl acetate | 700 |
| 50%* Aldehyde C 11 undecylic[1)] | 50 |
| Hexylcinnamic aldehyde | 1000 |
| Ethyl 2-methylpentanoate | 40 |
| 10%* α-Damascone[2)] | 150 |
| Geraniol brut | 150 |
| Geranyl nitrile | 20 |
| Habanolide ®[3)] | 250 |
| Hedione ® HC[4)] | 500 |
| Lilial ®[5)] | 300 |
| 10%* Isopropyl methylbutyrate | 10 |
| Methylnaphthylketone | 40 |
| Polysantol ®[6)] | 70 |
| Phenylhexanol | 100 |
| Orange essential oil | 150 |
| Romandolide ®[7)] | 250 |
| Terpineol | 130 |
| 10%* Triplal[8)] | 10 |
| Verdylate | 500 |
| Iso E Super[8)] | 100 |
| Yara-Yara | 20 |
| | 4500 |

*in dipropyleneglycol
[1)]origin: Firmenich SA, Geneva, Switzerland
[2)]1-(2,6,6-trimethyl-2-cyclohexen-1-yl)-2-buten-1-one; origin; Firmenich SA, Geneva, Switzerland
[3)]pentadecenolide; origin: Firmenich SA, Geneva, Switzerland
[4)]methyl dihydrojasmonate; origin: Firmenich SA, Geneva, Switzerland
[5)]origin: Givaudan, Vernier, Switzerland
[6)]3,3-dimethyl-5-(2',2',3'-trimethyl-3'-cyclopenten-1'-yl)-4-penten-2-ol; origin: Firmenich SA, Geneva, Switzerland
[7)](1S,1'R)-[1-(3',3'-dimethyl-1'-cyclohexyl)ethoxycarbonyl]methyl propanoate; origin: Firmenich SA, Geneva, Switzerland
[8)]origin: IFF, USA The addition of 1000 parts by weight of 4-cyclopentyl-2-methyl-2-butanol to this base composition, provided a new composition having a very nice fresh floral connotation. This effect was quite clear both upon using the composition to fragrance the detergent powder, and on the wet fabrics washed with the latter, which is quite rare for this type of notes.

Example 8

A perfuming base with a floral, herbaceous odor, intended for softeners, was prepared by admixing the following ingredients:

| Ingredient | Parts by weight |
|---|---|
| Benzyl acetate | 250 |
| cis-3-Hexenol acetate | 20 |
| Styrallyl acetate | 40 |
| Hexylcinnamic aldehyde | 200 |
| Artemisia essential oil | 30 |
| Methyl benzoate | 10 |

-continued

| Ingredient | Parts by weight |
|---|---|
| Camphor | 30 |
| Allyl caproate | 10 |
| L-Carvone | 20 |
| 10%* cis-3-Hexenol | 20 |
| 3,7-Dimethyl-6-octenenitrile | 15 |
| Allyl cyclohexylpropionate | 10 |
| Cyclosal | 10 |
| Estragol | 25 |
| Eucalyptol | 40 |
| Eugenol | 40 |
| 10%* Farenal[1)] | 50 |
| Diethyl 1,4-cyclohexanedicarboxylate[2)] | 25 |
| Geraniol | 40 |
| Habanolide ®[3)] | 100 |
| Hedione ®[4)] | 50 |
| 2-Phenoxyethyl isobutyrate | 250 |
| Lilial ®[5)] | 100 |
| Lorysia ®[6)] | 100 |
| 1%* Methyl octinecarbonate | 50 |
| 10%* Methylparacresol | 80 |
| Phenethylol | 250 |
| Terpineol ord | 80 |
| 10%* Triplal[7)] | 40 |
| Undecalactone gamma | 5 |
| Vert de Lilas | 10 |
| | 2000 |

*in dipropyleneglycol
[1)]origin: Haarmann & Reimer
[2)]origin: Firmenich SA, Geneva, Switzerland
[3)]pentadecenolide; origin: Firmenich SA, Geneva, Switzerland
[4)]methyl dihydrojasmonate; origin: Firmenich SA, Geneva, Switzerland
[5)]origin: Givaudan, Vernier, Switzerland
[6)]4-(1,1-dimethylethyl)-cyclohexanol acetate; origin: Firmenich SA, Geneva, Switzerland
[7)]origin: IFF, USA The addition of 1500 parts by weight of 4-cyclopentyl-2-methyl-2-butanol to the above-described base composition imparted to the latter a remarkable floral radiance, adding life, lift and richness to the composition.

What is claimed is:

1. A perfuming composition or a perfumed product comprising as active ingredient a compound of formula (I)

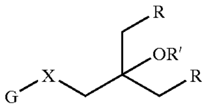
(I)

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, together with at least one perfuming co-ingredient, solvent or adjuvant of current use in perfumery.

2. The perfuming composition or a perfumed product according to claim 1, comprising as a perfuming ingredient a compound of formula (II)

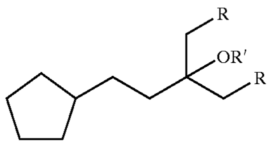
(II)

wherein the R groups represent, simultaneously or independently, a hydrogen atom or a methyl group and R' represents a hydrogen atom or an acetyl group.

3. The perfuming composition or perfumed article according to claim 2, wherein the perfuming ingredient is 4-cyclopentyl-2-methyl-2-butanol, 3-cyclopentyl-1,1-dimethylpropyl acetate or 5-cyclopentyl-3-ethyl-3-pentanol.

4. The perfuming composition or a perfumed product according to claim 1, in the form of a perfume or a cologne, a perfumed soap, a shower or bath gel, a shampoo, a body deodorant or antiperspirant, an ambient air deodorant, a liquid or solid detergent for textile treatment, a detergent composition or a cleaning product for dishes or various surfaces, a fabric softener or a cosmetic preparation.

5. The perfuming composition or the perfumed product according to claim 4, wherein the perfuming ingredient is a compound of formula (II)

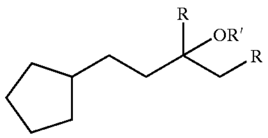
(II)

wherein the R groups represent, simultaneously or independently, a hydrogen atom or a methyl group and R' represents a hydrogen atom or an acetyl group.

6. A method to impart, enhance, improve or modify the odor properties of a perfuming composition or a perfumed product which method comprises adding to said composition or product as a perfuming ingredient a compound of formula (I)

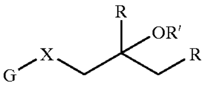
(I)

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, in an amount sufficient to impart, enhance, improve or modify the odor thereof with floral notes.

7. The method according to claim 6, wherein the perfuming ingredient is a compound of formula (II)

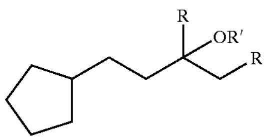
(II)

wherein the R groups represent, simultaneously or independently, a hydrogen atom or a methyl group and R' represents a hydrogen atom or an acetyl group.

8. The method according to claim 7, wherein the perfuming ingredient is 4-cyclopentyl-2-methyl-2-butanol, 3-cyclopentyl-1,1-dimethylpropyl acetate or 5-cyclopentyl-3-ethyl-3-pentanol.

9. The method according to claim 6, wherein the perfuming ingredient is added to a perfume or a cologne, a perfumed soap, a shower or bath gel, a shampoo, a body deodorant or antiperspirant, an ambient air deodorant, a liquid or solid detergent for textile treatment, a detergent composition or a cleaning product for dishes or various surfaces, a fabric softener or a cosmetic preparation.

10. A compound of formula (I)

(I)

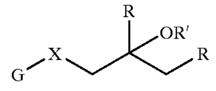

wherein the R groups represent, simultaneously or independently, a hydrogen atom or a methyl group, R' represents a hydrogen atom or an acetyl group, G represents a cyclopentyl or a cyclopentenyl radical, and X represents a oxygen atom or a $CH_2$ group, provided that 4-cyclopentyl-2-methyl-2-butanol is excluded.

11. The compound according to claim 10, having formula (II)

(II)

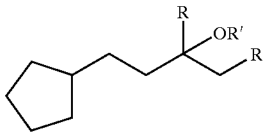

wherein the R groups represent, simultaneously or independently, a hydrogen atom or a methyl group and R' represents a hydrogen atom or an acetyl group.

12. The compound according to claim 10, specifically as 3-cyclopentyl-1,1-dimethylpropyl acetate, 5-cyclopentyl-3-ethyl-3-pentanol, 4-(2-cyclopenten-1-yl)-2-methyl-2-butanol or 1-(cyclopentyloxy)-2-methyl-2-propanol.

* * * * *